(12) United States Patent
Sarkis Mardiguian

(10) Patent No.: US 7,462,735 B2
(45) Date of Patent: Dec. 9, 2008

(54) AMINO ACID DIAMIDES IN NON α POSITION WHICH ARE USEFUL AS ADJUVANTS FOR ADMINISTRATION OF BIOLOGICAL ACTIVE AGENTS

(75) Inventor: Jean Sarkis Mardiguian, Madrid (ES)

(73) Assignee: Laboratorios Farmaceuticos Rovi, S.A., Madrid (ES)

( * ) Notice: Subject to any disclaimer, the term of this patent is extended or adjusted under 35 U.S.C. 154(b) by 160 days.

(21) Appl. No.: 10/563,994

(22) PCT Filed: Jul. 23, 2004

(86) PCT No.: PCT/ES2004/000346

§ 371 (c)(1), (2), (4) Date: Jul. 14, 2006

(87) PCT Pub. No.: WO2005/012230

PCT Pub. Date: Feb. 10, 2005

(65) Prior Publication Data

US 2007/0191302 A1     Aug. 16, 2007

(30) Foreign Application Priority Data

Jul. 28, 2003   (ES)   ................................ 200301781

(51) Int. Cl.
*C07C 229/00* (2006.01)
*A61K 31/715* (2006.01)
*A61K 31/727* (2006.01)
*A61K 31/195* (2006.01)

(52) U.S. Cl. ............................ 562/450; 514/54; 514/56; 514/563

(58) Field of Classification Search ................ 562/450; 514/54, 56, 563

See application file for complete search history.

(56) References Cited

U.S. PATENT DOCUMENTS

| 6,525,020 | B2 | 2/2003 | Leone-Bay et al. |
| 6,541,203 | B2 * | 4/2003 | Mitchison ..................... 435/6 |
| 2002/0006614 | A1 | 1/2002 | Michison |
| 2004/0110839 | A1 | 6/2004 | Leone-Bay et al. |

FOREIGN PATENT DOCUMENTS

| WO | 00/07979 | | 2/2000 |
| WO | 03/015774 | A1 | 2/2003 |

* cited by examiner

*Primary Examiner*—Sikarl A Witherspoon
(74) *Attorney, Agent, or Firm*—Rick Matos; Innovar, L.L.C.

(57) ABSTRACT

Amino acid diamides in non α position of formula (1), wherein $R_1$ is selected from amongst the group consisting of the functional groups alkyl, halogen, $NO_2$, OH, $OCH_3$ alone or associated and $R_2$ is selected from the group consisting of functional groups H, alkyl, halogen, $NO_2$, OH, $OCH_3$, which are useful as adjuvants for the administration of biological active agents, as well as pharmaceutical compositions containing these diamides of formula (1) and the use thereof for the manufacture of antithrombotic medications and for the manufacture of a medication for the treatment of a disease selected from amongst the group consisting of inflammation, cancer and allergy.

15 Claims, 2 Drawing Sheets

AMINO ACID DIAMIDES IN NON α POSITION WHICH ARE USEFUL AS ADJUVANTS FOR ADMINISTRATION OF BIOLOGICAL ACTIVE AGENTS

FIELD OF THE INVENTION

The present invention relates to new amino acid diamides in non α position which are useful as adjuvants for administration of biological active ingredients. The compounds under the invention facilitate the oral, intraduodenal, intracolonic and pulmonary administration of heparin, low-molecular-weight heparins, very-low-molecular-weight heparins, and other glycosaminoglycans and derivatives.

BACKGROUND OF THE INVENTION

Heparin is currently used in parenteral administration for the prevention and treatment of deep venous thrombosis. Heparin and related derivatives are ineffective or are destroyed in the gastrointestinal tract by acid or enzymatic hydrolysis. In addition, the size and ionic charge of the molecules could prevent absorption.

Various adjuvants (for example, non-ionic surfactants) have been used to improve the oral absorption of heparin. Recently, modified amino acids have been used to facilitate the administration of various biological agents, in particular heparin (WO 98/34632, WO 01/51454, WO 97/36480).

These compounds are essentially derived from 4-aminophenylbutyric acid:

Structure A

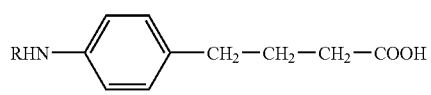

and various amides such as:

Structure B

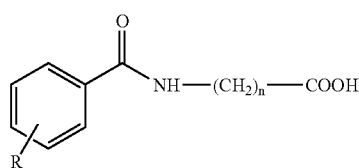

In particular, the following derivatives

Structure C

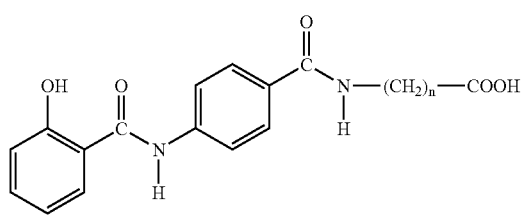

Primarily those derivatives relative to n=2 and n=5 (WO 97/36480) are claimed as agents that facilitate the oral absorption of biological products.

DESCRIPTION OF THE INVENTION

In the framework of its research on the oral absorption of heparin, the applicant has discovered a new family of chemical products that facilitate and considerably increase the oral absorption of heparin and its low-molecular-weight derivatives, particularly by colonic administration.

These products have the following structure

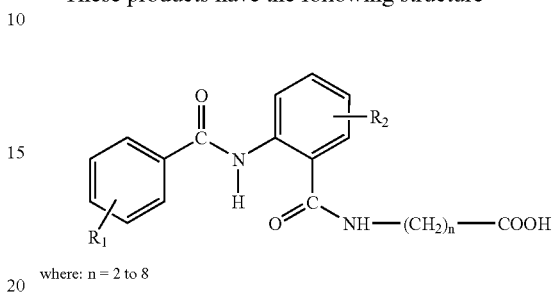

where: n = 2 to 8 wherein $R_1$ is selected from amongst the group consisting of functional groups alkyl, halogen, $NO_2$, OH, $OCH_3$ either alone or associated and $R_2$ is selected from the group consisting of functional groups H, alkyl, halogen, $NO_2$, OH, $OCH_3$.

These products are new. The research conducted by the applicant has demonstrated the originality of structure. In effect, the applicant has been able to show that the above mentioned products, structure C, n=3 (example 1) and n=5 (example 2), synthesised by the applicant have no effect on colonic absorption of a low-molecular-weight heparin (bemiparin) in the rat. Likewise, the products that have the structure D, n=3 (example 3)

Structure D

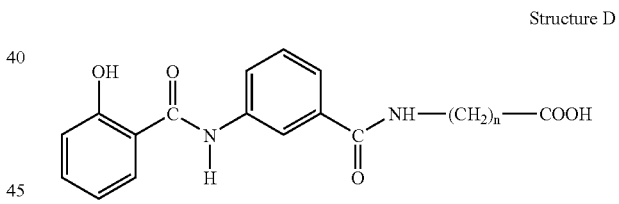

synthesised by the applicant have no effect on the colonic absorption of bemiparin (see Table 1).

Table 1 shows the anti-Xa activity/ml in plasma after intracolonic administration in rat of Bemiparin and of the association of Bemiparin along with compounds from the examples 1, 2 and 3, as shown therein:

TABLE 1

| Treatment | Admin. route | Dosage (mg/kg) | Post-administration time (h) | | |
|---|---|---|---|---|---|
| | | | 0.5 | 2 | 4 |
| Bemiparin | Intracolonic | 30 | 0.103 | 0.222 | 0.345 |
| Bemi. + ex. 1 | Intracolonic | 30 + 30 | 0.299 | 0.196 | 0.147 |
| Bemi. + ex. 2 | Intracolonic | 30 + 30 | 0.367 | 0.193 | 0.111 |
| Bemi. + ex. 3 | Intracolonic | 30 + 30 | 0.520 | 0.316 | 0.240 |

These results tend to show the importance of the hydrogen bond between the O and H atoms of the invention products.

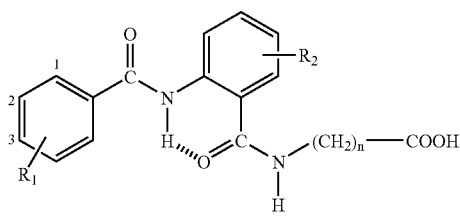

FIG. 3 shows the intracolonic absorption in the rat of the association of the pharmaceutical composition RO-14 with the product of example 4.

A series of examples is provided below in order to clarify the invention, without limiting the scope of the invention. These examples describe the procedure for the preparation of compounds 1 to 22 indicated below, as well as their intracolonic absorption-enhancing effect of the low-molecular-weight heparin, Bemiparin.

Another characteristic of the invention relates to the importance of the nature and position of the $R_1$ substituent as well as the chain length (n value).

The applicant has also discovered that the derivatives that have the Cl or $NO_2$ substituents in position 3 are at least as active as the derivatives that have an OH in position 1.

Among the invention products, the preferred compounds are those that correspond to n=3 and to the OH (example 4), Cl (example 17), $NO_2$ (example 11) substituents.

The invention products are usable in the form of an acid or in the form of a soluble salt, biologically acceptable, or of a pharmaceutical composition containing a heparin or a heparin derivative (ester, amide, oligosaccharides, etc.) as well as an adjuvant known for its favourable action (polyethylene glycol, alginate, chitosan and derivatives, propylene glycol, carbopol, etc.).

One of the preferred compositions consists of associating one of the products described above with a low-molecular-weight heparin such as bemiparin for an oral use in the prevention and treatment of venous and arterial thrombosis.

Another application of the invention products consists of associating them with any non-anticoagulant derivative of heparin for an oral utilization in conditions such as inflammation, allergy and cancer.

In general, the invention products enhance the oral absorption, particularly by the colonic route, of glycosaminoglycans and glycosaminoglycan oligosaccharides.

The properties of the invention products have been investigated in an experimental model described below that consists of measuring the intracolonic absorption in the rat of a low-molecular-weight heparin, bemiparin, with a mean molecular mass of around 3,500 daltons and an anti-Xa activity of around 100 units/mg.

The results obtained show, in particular for the products of examples 4 (see FIG. 1), 11 and 17 (see FIG. 2), a strong increase in the absorption of bemiparin measured by the plasma anti-Xa activity.

Figure 1:
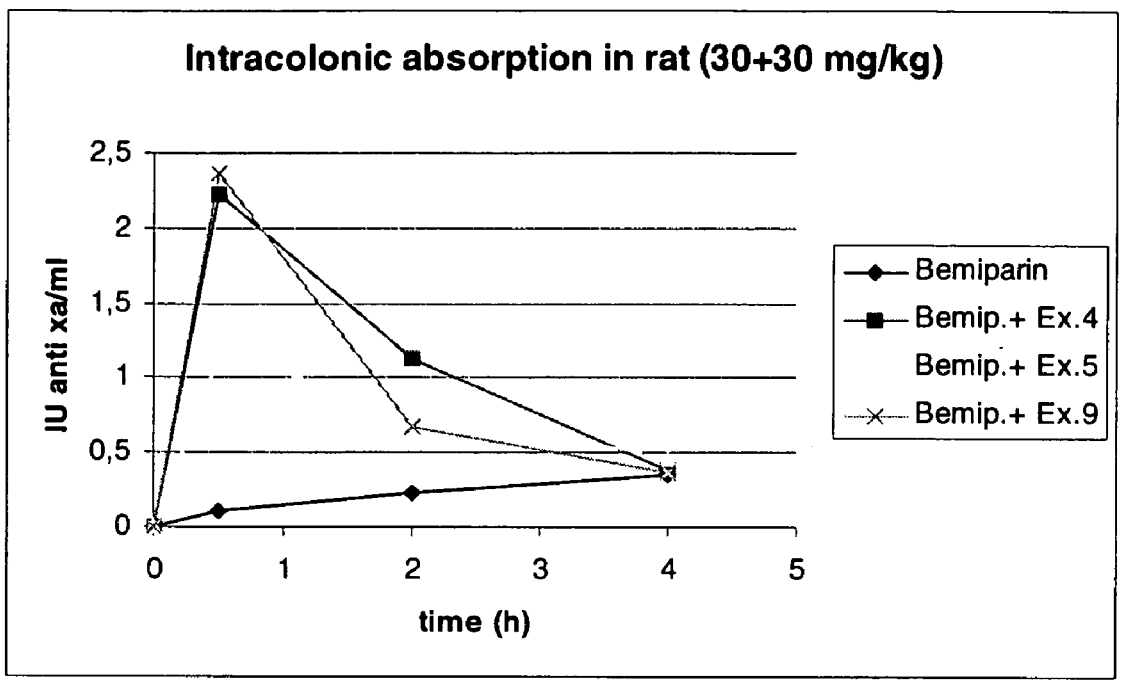
FIG. 1 shows the intracolonic absorption in the rat of bemiparin and of the compounds of examples 4, 5 and 9, which are shown below.
Figure 2:
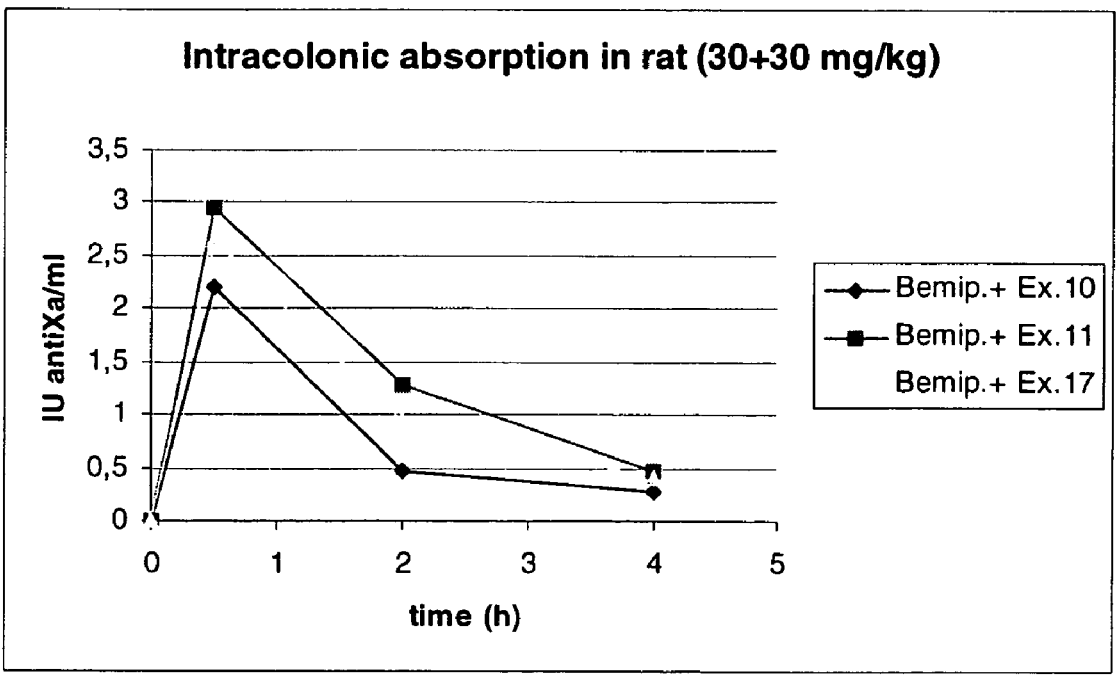
FIG. 2 shows the intracolonic absorption in the rat of the compounds of examples 10, 11 and 17, which are shown below.
Figure 3:
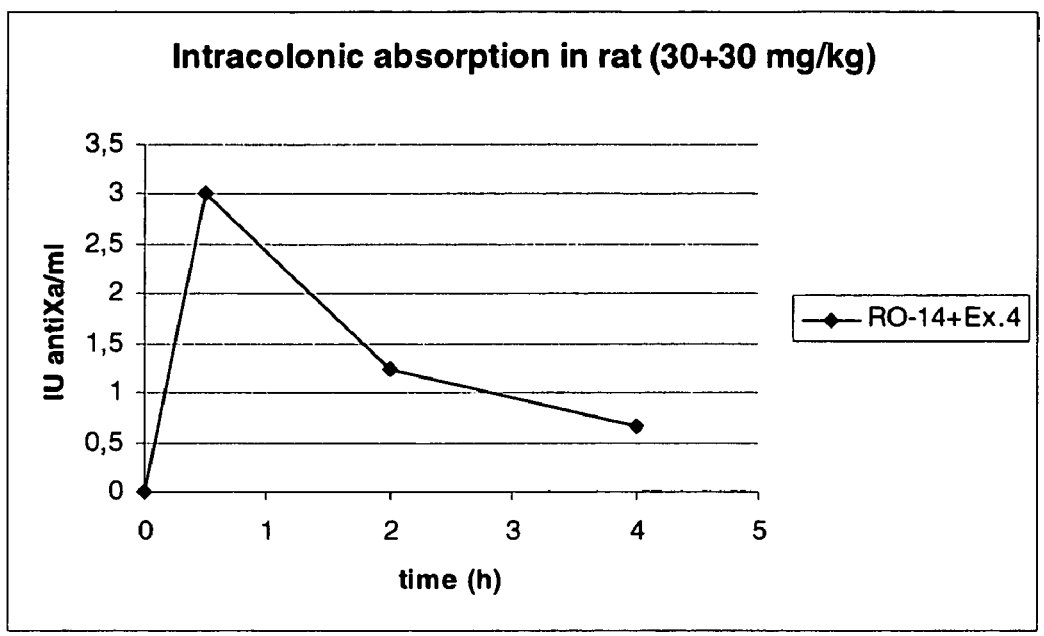

Another advantage of the invention products and of their interest as agents that increase the oral absorption of oligosaccharides derived from heparin has been demonstrated by the study of the intracolonic absorption of a very-low-molecular-weight heparin, RO-14, (2,500 daltons, 80 to 100 units anti-Xa/mg). The pharmaceutical composition RO-14+product of example 4 (see FIG. 3) shows a high, long-lasting anti-Xa activity.

EXAMPLE 1

4-[4-(hydroxybenzoylamino)benzoylamino]butanoic acid. (compound 1)

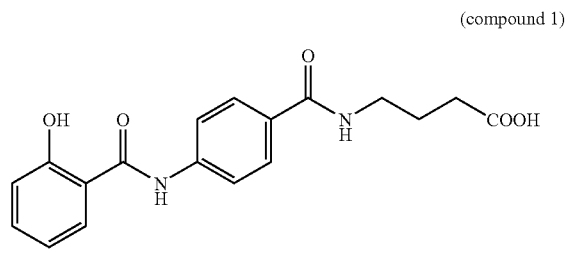

(compound 1)

To a solution of 4.41 g (18.69 mmol) of methyl 4-(4-aminobenzoylamino)butanoate dissolved in 80 ml of ethyl acetate, very slowly add 2.49 g (15.97 mmol) of 2-hydroxybenzoyl chloride dissolved in 10 ml of ethyl acetate. Then add 1.61 g (15.97 mmol) of triethylamine and keep the reaction mixture at room temperature for 24 hours. Eliminate the solvent at low pressure, add 40 ml of 10% NaOH to the crude product and continue stirring the mixture until the solid has completely disappeared. Immediately acidify with concentrated hydrochloric acid, filter the resulting solid and wash several times with water. Purify the reaction product by recrystallization (EtOH/$H_2O$). This yields 1.48 g (27%) of 4-[4-(2-hydroxybenzoylamino)benzoylamino]butanoic acid as a white solid.

M.P.: 211-213° C. IR (KBr): ν3360, 2970, 2680, 1700, 1665, 1620, 1540, 1510, 855, 770, 750, 695 cm$^{-1}$ $^1$H NMR (DMSO, 400 MHz): δ 1.75 (m, 2 H, —$CH_2$—), 2.27 (t, 2 H, J=7.2 Hz, —$CH_2$—CO—), 3.27 (m, 2 H, —$CH_2$—N—), 6.97 (m, 2 H, aromatic), 7.43 (m, 1 H, aromatic), 7.79 (d, 2 H, J=8.5 Hz, aromatic), 7.85 (d, 2 H, J=8.5 Hz, aromatic), 7.94 (m, 1 H, aromatic), 8.39 (t, 1 H, J=5.3 Hz, —NH—$CH_2$—), 10.51 (s, 1 H, —NH-Ph) ppm $^{13}$C NMR (DMSO, 100 MHz): 24.6, 31.6, 38.6, 117.2, 117.9, 119.1, 119.8, 127.9, 129.3, 129.9, 133.7, 140.7, 158.0, 165.6, 166.4, 174.2 ppm MS m/z (%): 342 (M$^+$, 4), 324 (5), 239 (19), 204 (18), 168 (21), 120 (100), 92 (19), 65 (33) Elemental analysis of $C_{18}H_{18}N_2O_5$ Calculated: % C=63.15; % H=5.30; % N=8.18. Found: % C=63.10; % H=5.32; % N=8.04.

EXAMPLE 2

6-[4-(2-hydroxybenzoylamino)benzoylamino]hexanoic acid. (compound 2)

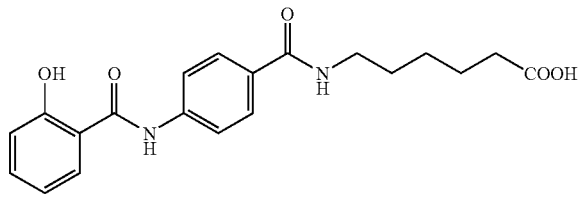
(compound 2)

To a solution of 2.81 g (10.64 mmol) of methyl 6-(4-aminobenzoylamino)hexanoate dissolved in 50 ml of acetonitrile, very slowly add 1.42 g (9.10 mmol) of 2-hydroxybenzoyl chloride dissolved in 5 ml of acetonitrile. Then add 0.92 g (9.10 mmol) of triethylamine and keep the reaction mixture at room temperature for 24 hours. Eliminate the solvent at low pressure, add 30 ml of 10% NaOH to the crude product and continue stirring the mixture until the solid has completely disappeared. Immediately acidify with concentrated hydrochloric acid, filter the resulting solid and wash several times with water. Purify the reaction product by recrystallization (EtOH/H$_2$O). This yields 1.11 g (33%) of 6-[4-(2-hydroxybenzoylamino)benzoylamino]hexanoic acid as a white solid.

M.P.: 201-203° C. IR(KBr): ν3330, 3050, 2950, 2680, 2570, 1700, 1675, 1600, 1540, 855, 770, 750 cm$^{-1}$ $^1$H NMR (DMSO, 400 MHz): δ 1.32 (m, 2 H, —CH$_2$—CH$_2$—CH$_2$—), 1.51 (m, 4 H, —CH$_2$—CH$_2$—CH$_2$—), 2.20 (t, 2 H, J=7.3 Hz, —CH$_2$—CO—), 3.23 (m, 2 H, —CH$_2$—N—), 6.97 (m, 2 H, aromatic), 7.43 (m, 1 H, aromatic), 7.78 (d, 2 H, J=8.5 Hz, aromatic), 7.84 (d, 2 H, J=8.5 Hz, aromatic), 7.93 (m, 1 H, aromatic), 8.35 (t, 1 H, J=5.1 Hz, —NH—CH$_2$—), 10.51 (s, 1 H, —NH-Ph), 11.62 (s, 1 H, —OH), 11.95 (s, 1 H, —COOH) ppm $^{13}$C NMR (DMSO, 100 MHz): δ 14.2, 24.5, 25.5, 28.6, 34.1, 60.3, 68.5, 114.3, 125.9, 164.1, 173.5 ppm MS m/z (%) 263 (M-18, 3), 236 (4), 218 (2), 172 (5), 143 (20), 115 (16), 97 (49), 69 (100), 55 (49), 41 (65) Elemental analysis of C$_{20}$H$_{22}$N$_2$O$_5$ Calculated: % C=64.85; % H=5.99; % N=7.56. Found: % C=64.51; % H=5.86; % N=7.45

EXAMPLE 3

4-[3-(2-hydroxybenzoylamino)benzoylamino]butanoic acid. (compound 3)

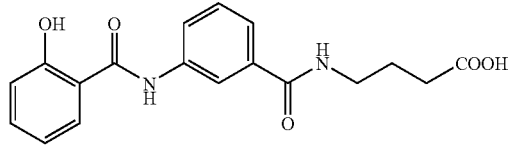
(compound 3)

To a solution of 2.60 g (11.00 mmol) of methyl 4-(3-aminobenzoylamino)butanoate dissolved in 25 ml of ethyl acetate, very slowly add 1.40 g (10.00 mmol) of 2-hydroxybenzoyl chloride dissolved in 5 ml of ethyl acetate. Then add 1.00 g (10.00 mmol) of Et$_3$N (triethylamine) and keep the reaction mixture at room temperature for 24 hours. Eliminate the solvent at low pressure, add 40 ml of 10% NaOH to the crude product and continue stirring the mixture until the oil has completely disappeared. Immediately acidify with concentrated HCl, filter the resulting solid and wash several times with water. Purify the reaction product by recrystallization (EtOH/H$_2$O). This yields 1.60 g (48%) of 4-[3-(2-hydroxybenzoylamino) benzoylamino]butanoic acid as a white solid.

M.P.: 172-174° C. IR(ATR): ν 3291, 2940, 1714, 1611, 1551, 1455, 1335, 1232, 1214, 878, 817, 735 cm$^{-1}$ $^1$H NMR (DMSO, 400 MHz): δ 1.77 (q, 2 H, J=7.0 Hz, —CH$_2$—), 2.28 (t, 2 H, J=7.4 Hz, —CH$_2$—CO—), 3.28 (m, 2 H, —CH$_2$—N—), 6.97 (m, 2 H, aromatic), 7.43 (m, 2 H, aromatic), 7.59 (m, 1 H, aromatic), 7.87 (m, 1 H, aromatic), 7.98 (m, 1 H, aromatic) 8.12 (m, 1 H, aromatic), 8.50 (t, 1 H, J=5.0 Hz, —NH—CH$_2$—), 10.50 (s,1H, —NH—) ppm $^{13}$C NMR (DMSO, 100 MHz): δ 24.5, 31.2, 38.7, 117.3, 117.4, 119.1, 120.2, 122.7, 123.5, 128.6, 129.1, 133.8, 135.4, 138.2, 158.5, 166.1, 166.7, 174.2 ppm MS m/z (%): 238 (M$^+$-104, 61), 210 (3), 186 (2), 160 (3), 137 (9), 119 (100), 120 (30), 92 (50), 91 (12), 65 (31) Elemental analysis of C$_{18}$H$_{18}$N$_2$O$_5$ Calculated: % C=63.14; % H=5.31; % N=8.18. Found: % C=63.01; % H=5.23; % N=8.21.

EXAMPLE 4

4-[2-(2-hydroxybenzoylamino)benzoylamino]butanoic acid. (compound 4)

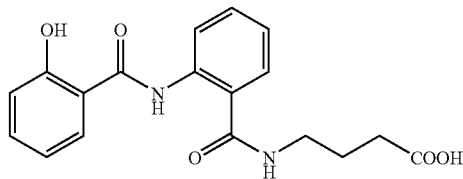
(compound 4)

To a suspension of 20.36 g (91.71 mmol) of 4-(2-aminobenzoylamino)butanoic acid in 200 ml of dry methylene chloride, add 42.33 g (391.92 mmol) of trimethylsilyl chloride and allow the reaction to reflux for 5 hours. Then place the flask in an ice bath and add 11.87 g (117.57 mmol) of triethylamine and a solution of 15.52 g (78.38 mmol) of acetylsalicyloyl chloride dissolved in 20 ml of dry methylene chloride. Allow the reaction to stir for 30 minutes in an ice bath and 24 hours at room temperature. Eliminate the solvent at low pressure, add 200 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/H$_2$O). This yields 21.66 g (81%) of 4-[2-(2-hydroxy-benzoylamino)benzoylamino]butanoic acid as a white solid.

M.P.: 173-174° C. IR(ATR): ν 3322, 2925, 2852, 1688, 1652, 1633, 1597, 1529, 1448, 1260, 1228, 756 cm$^{-1}$ $^1$H NMR (DMSO, 400 MHz): δ1.76 (q, 2 H, J=7.0 Hz, —CH$_2$—), 2.28 (t, 2 H, J=7.3 Hz, —CH$_2$—CO—), 3.27 (m, 2 H, —CH$_2$—N—), 6.96 (m, 2 H, aromatic), 7.20 (m, 1 H, aromatic), 7.42 (m, 1 H, aromatic), 7.50 (m, 1 H, aromatic), 7.68 (m, 1 H, aromatic), 7.83 (m, 1H, aromatic) 8.48 (m, 1 H, aromatic), 8.50 (t, 1 H, J=5.0 Hz, —NH—CH$_2$—), 11.62 (S$_{broad}$, 1H, —OH), 12.03 (S$_{broad}$, 1H, —COOH), 12.19 (s, 1

H, —NH-Ph) ppm $^{13}$C NMR (DMSO, 200 MHz): δ 24.2, 31.1, 38.9, 117.2, 117.9, 119.3, 121.7, 123.1, 123.3, 128.1, 129.2, 131.3, 133.7, 137.8, 158.1, 165.5, 168.1, 174.2 ppm MS m/z (%): 342 (M$^+$, 5), 265 (4), 239 (100), 222 (11), 121 (50), 120(64), 119 (62), 92 (54), 77 (10), 65 (53), 39 (39) Elemental analysis of $C_{18}H_{18}N_2O_5$ Calculated: % C=63.15; % H=5.30; % N=8.18. Found: % C=63.15; % H=5.38; % N=8.15.

EXAMPLE 5

5-[2-(2-hydroxybenzoylamino)benzoylamino]pentanoic acid. (compound 5)

(compound 5)

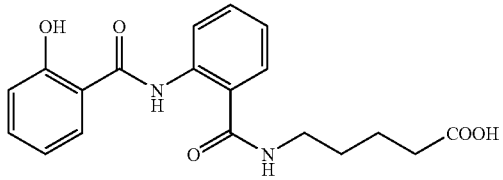

To a suspension of 1.61 g (6.81 mmol) of 5-(2-aminobenzoylamino)pentanoic acid in 20 ml of dry methylene chloride, add 1.41 g (11.94 mmol) of trimethylsilyl chloride and allow the reaction to reflux for 5 hours. Then place the flask in an ice bath and add 0.88 g (8.73 mmol) of triethylamine and a solution of 1.15 g (5.82 mmol) of acetylsalicyloyl chloride dissolved in 5 ml of dry methylene chloride. Allow the reaction to stir for 30 minutes in an ice bath and 24 hours at room temperature. Eliminate the solvent at low pressure, add 20 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/H$_2$O). This yields 1.26 g (61%) of 5-[2-(2-hydroxybenzoylamino) benzoyl-amino]pentanoic acid as a white solid.

M.P.: 168-170° C. IR(ATR): ν 3310, 1698, 1648, 1626, 1597, 1521, 1269, 1223, 1139, 746 cm$^{-1}$ $^1$H NMR (400 MHz, DMSO): δ1.54 (m, 4H, —CH$_2$—CH$_2$—CH$_2$—CH$_2$—), 2.21 (t, 2 H, J=7.2 Hz, —CH$_2$—CO), 3.26 (m, 2 H, —CH$_2$—N—), 6.97 (m, 2 H, aromatic), 7.18 (m, 1 H, aromatic), 7.40 (m, 1 H, aromatic), 7.51 (m, 1 H, aromatic), 7.67 (m, 1 H, aromatic), 7.84 (m, 1 H, aromatic), 8.47 (m, 1 H, aromatic), 8.72 (t, 1 H, J=5.4 Hz, —NH—CH$_2$—), 11.62 (s, 1 H, —OH), 11.98 (s, 1 H, —COOH), 12.18 (s, 1 H, —NH-Ph) ppm $^{13}$C NMR (200 MHz, DMSO): δ 22.0, 28.3, 33.3, 38.9, 117.2, 118.0, 119.3, 121.74, 123.2, 123.5, 128.0, 129.3, 131.3, 133.7, 137.8, 158.0, 165.5, 168.0, 174.4 ppm MS m/z (%): 356 (M$^+$, 1), 337 (9), 239 (72), 119 (100), 99 (18), 92 (59), 77 (15), 65 (48), 41 (25) Elemental analysis of $C_{19}H_{20}N_2O_5$ Calculated: % C=64.04; % H=5.66; % N=7.86. Found: % C=63.90; % H=5.69; % N=7.75.

EXAMPLE 6

8-[2-(2-hydroxybenzoylamino)benzoylamino]octanoic acid. (compound 6)

(compound 6)

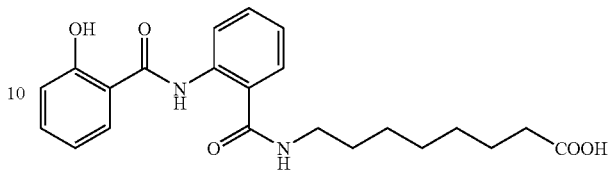

To a suspension of 2.00 g (7.20 mmol) of 8-(2-aminobenzoylamino)octanoic acid in 25 ml of dry methylene chloride, add 1.36 g (12.60 mmol) of trimethylsilyl chloride and allow the reaction to reflux for 5 hours. Then place the flask in an ice bath and add 0.93 g (9.22 mmol) of triethylamine and a solution of 1.21 g (6.15 mmol) of acetylsalicyloyl chloride dissolved in 5 ml of dry methylene chloride. Allow the reaction to stir for 30 minutes in an ice bath and 24 hours at room temperature. Eliminate the solvent at low pressure, add 20 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/H$_2$O). This yields 1.41 g (58%) of 8-[2-(2-hydroxybenzoylamino)benzoylamino]octanoic acid as a white solid.

M.P.: 124-125° C. IR(ATR): ν 3310, 2931, 2855, 1698, 1654, 1627, 1585, 1526, 1495, 1448, 1409, 1361, 1315, 1268, 1222, 1196, 1168 cm$^{-1}$ $^1$H NMR (400 MHz, DMSO): δ1.25 (m, 6H, —CH$_2$—CH$_2$—CH$_2$—CH$_2$—CH$_2$—CH$_2$—CH$_2$—), 1.46 (m, 4H, —CH$_2$—CH$_2$—CH$_2$—CH$_2$—CH$_2$CH$_2$—), 2.14 (t, 2 H, J=7.5 Hz, —CH$_2$—CO), 3.23 (m, 2 H, —CH$_2$—N—), 6.95 (m, 2 H, aromatic), 7.18 (m, 1 H, aromatic), 7.41 (m, 1 H, aromatic), 7.50 (m, 1 H, aromatic), 7.65 (m, 1 H, aromatic), 7.84 (m, 1 H, aromatic), 8.44 (m, 1 H, aromatic), 8.67 (t, 1 H, J=5.7 Hz, —NH—CH$_2$—), 11.61 (s, 1H, —OH), 11.90 (s, 1 H, —COOH), 12.13 (s, 1 H, —NH-Ph) ppm $^{13}$C NMR (200 MHz, DMSO): δ24.5, 26.4, 28.50, 28.52, 28.8, 33.6, 39.2, 117.2, 117.9, 119.3, 121.8, 123.2, 123.8, 128.0, 129.2, 131.2, 133.7, 137.7, 158.1, 165.5, 167.9, 174.5 ppm MS m/z (%): 398 (M$^+$, 1), 379 (3), 351 (2), 278 (5), 251 (6), 239 (94), 197 (9), 137 (11), 119 (100), 100 (17), 92 (51), 77 (8), 65 (37), 41 (20) Elemental analysis of $C_{19}H_{20}N_2O_5$ Calculated: % C=66.32; % H=6.58, % N=7.03. Found: % C=66.03; % H=6.47; % N=7.05.

EXAMPLE 7

6-[2-(2-hydroxybenzoylamino)benzoylamino]hexanoic acid. (compound 7)

(compound 7)

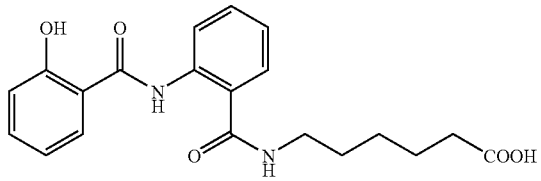

To a suspension of 0.30 g (1.20 mmol) of 6-(2-aminobenzoylamino)hexanoic acid in 5 ml of dry methylene chloride, add 0.23 g (2.10 mmol) of trimethylsilyl chloride and allow the reaction to reflux for 5 hours. Then place the flask in an ice bath and add 0.15 g (1.53 mmol) of triethylamine and a solution of 0.20 g (2.05 mmol) of 2-acetylsalicyloyl chloride dissolved in 5 ml of dry methylene chloride. Allow the reaction to stir for 30 minutes in an ice bath and 24 hours at room temperature. Eliminate the solvent at low pressure, add 10 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/H$_2$O). This yields 0.24 g (62%) of 6-[2-(2-hydroxybenzoylamino)benzoylamino]hexanoic as a white solid.

M.P.: 165-167° C. IR(ATR): ν 3348, 2923, 2853, 1688, 1595, 1523, 1493, 1414, 1360, 1272, 903, 815, 759 cm$^{-1}$ $^1$H-NMR (400 MHz, DMSO): δ1.31 (m, 2 H, —CH$_2$—CH$_2$—CH$_2$—), 1.51 (m, 4H, —CH$_2$—CH$_2$—CH$_2$—CH$_2$CH$_2$—), 2.17 (t, 2 H, J=7.4 Hz, —CH$_2$—CO—), 3.24 (m, 2H, —CH$_2$—NH—), 6.96 (m, 2 H, aromatic), 7.18 (m, 1 H, aromatic), 7.41 (m, 1 H, aromatic), 7.50 (m, 1 H, aromatic), 7.66 (m, 1 H, aromatic), 7.84 (m, 1 H, aromatic), 8.46 (m, 1 H, aromatic), 8.69 (S$_{broad}$, 1H, —NH—CH$_2$—), 11.61 (s, 1 H, —OH), 11.93 (s, 1 H, —COOH), 12.16 (s, 1H, —NH-Ph) ppm $^{13}$C NMR (200 MHz, DMSO): δ 24.2, 26.0, 28.5, 33.6, 39.1, 117.2, 118.0, 119.3, 121.8, 123.2, 123.7, 128.0, 129.3, 131.2, 133.7, 137.7, 158.0, 165.4, 167.9, 174.4, ppm MS m/z (%): 352 (M$^+$–18, 3), 351 (4), 265 (3), 251 (9), 239 (56), 211 (6), 132 (7), 119 (100), 102 (5), 92 (62), 77 (15), 65 (52), 41 (26) Elemental analysis of C$_{20}$H$_{22}$N$_2$O$_5$ Calculated: % C=64.85; % H=5.99; % N=7.56. Found: % C=64.57; % H=5.93; % N=7.57.

EXAMPLE 8

4-[2-(2-nitrobenzoylamino)benzoylamino]butanoic acid. (compound 8)

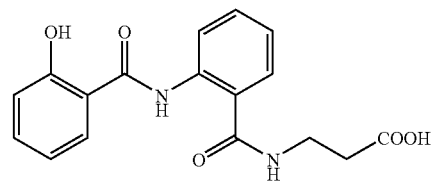

(compound 8)

To a suspension of 3.90 g (17.50 mmol) of 4-(2-aminobenzoylamino)butanoic acid in 40 ml of dry ethyl acetate, add 3.26 g (17.56 mmol) of 2-nitrobenzoyl chloride dissolved in 5 ml of dry ethyl acetate and 1.76 g of triethylamine. Allow the reaction mixture to stir for 24 hours at room temperature. Eliminate the solvent at low pressure, add 30 ml of 10% NaOH to the crude product and continue stirring the mixture until the solid has completely disappeared. Immediately acidify with concentrated HCl and extract the product with ethyl acetate. Eliminate the solvent at low pressure and recombine the crude product with dry ether, obtaining a white solid. Purify the reaction product by recrystallization (EtOH/H$_2$O). This yields 3.34 g (51%) of 4-[2-(2-nitrobenzoylamino)benzoylamino]butanoic acid as a white solid.

M.P.: 142-144° C. IR(ATR): ν 3348, 2923, 2853, 1688, 1595, 1523, 1493, 1414, 1360, 1272, 903, 815, 759 cm$^{-1}$ $^1$H-NMR (400 MHz, DMSO): δ1.73 (m, 2 H, —CH$_2$—CH$_2$—CH$_2$—), 2.26 (t, 2 H, J=7.0 Hz, —CH$_2$—CO—), 3.24 (m, 2 H, —CH$_2$—NH—), 7.24 (m, 1 H, aromatic), 7.56 (m, 1 H, aromatic), 7.80 (m, 4H, aromatic), 8.10 (m, 1 H, aromatic), 8.38 (m, 1 H, aromatic), 8.82 (S$_{broad}$, 1H, —NH—CH$_2$—), 12.02 (s, 1 H, —COOH), 12.06 (s, 1 H, —NH-Ph) ppm $^{13}$C NMR (200 MHz, DMSO): δ 24.1, 31.0, 38.6, 120.8, 121.6, 123.6, 124.6, 128.2, 128.3, 131.5, 131.98, 132.02, 134.1, 138.3, 147.1, 163.3, 168.1, 174.1 ppm MS m/z (%): 371 ($^+$, 4), 353 (6), 268 (26), 236 (49), 208 (36), 150 (54), 134 (100), 120 (55), 119 (55), 104 (39), 90 (47), 76 (57), 44 (58) Elemental analysis of C$_{18}$H$_{17}$N$_3$O$_6$ Calculated: % C=58.22; % H=4.61; % N=11.32. Found: % C=58.15; % H=4.55; % N=11.35.

EXAMPLE 9

3-[2-(2-hydroxybenzoylamino)benzoylamino]propanoic acid. (compound 9)

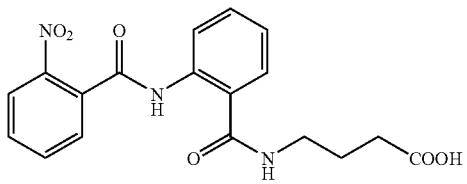

(compound 9)

To a suspension of 0.5 g (2.40 mmol) of 3-(2-aminobenzoylamino)propanoic acid in 10 mL of dry methylene chloride, add 0.45 g (4.20 mmol) of trimethylsilyl chloride and allow the reaction to reflux under argon during 2 hours. Then place the flask in an ice bath and add 0.31 g (3.07 mmol) of triethylamine and a solution of 0.40 g (2.05 mmol) of 2-acetylsalicycoyl chloride dissolved in 5 ml of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and ether. Purify the reaction product by recrystallization (EtOH/H$_2$O). This yields 0.37 g (56%) of 3-[2-(2-hydroxybenzoylamino)benzoylamino]propanoic acid as a white solid.

M.P.: 200-202° C. IR(ATR): ν 3331, 3051, 2657, 1718, 1649, 1626, 1593, 1523, 1269, 1225, 904, 853, 749 cm$^{-1}$ $^1$H-NMR (400 MHz, DMSO): δ 2.52 (t, 2 H, J=7.4 Hz, —CH$_2$—CO—), 3.46 (m, 2 H, —CH$_2$—N—), 6.97 (m, 2 H, aromatic), 7.18 (m, 1 H, aromatic), 7.41 (m, 1 H, aromatic), 7.51 (m, 1 H, aromatic), 7.65 (m, 1 H, aromatic), 7.85 (m, 1 H, aromatic), 8.45 (m, 1 H, aromatic), 8.79 (S$_{broad}$, 1 H, —NH—CH$_2$—), 11.61 (s, 1H, —OH), 12.15 (s, 1 H, —COOH), 12.25 (s, 1 H, —NH-Ph), ppm $^{13}$C NMR (200 MHz, DMSO): δ 35.4, 35.5, 117.2, 118.02, 119.3, 121.7, 123.1, 123.2, 128.0, 129.4, 131.4, 131.7, 137.8, 157.9, 165.3, 168.1, 172.7 ppm MS m/z (%): 328 (M$^+$, 6), 293 (2), 250 (5), 239 (100), 208 (20), 119 (65), 92 (50), 65 (60), 44 (42) Elemental analysis of C$_{17}$H$_{16}$N$_2$O$_5$ Calculated: % C=62.19; % H=4.91; % N=8.53. Found: % C=61.82; % H=4.72; % N=8.39.

EXAMPLE 10

2-[2-(2-hydroxybenzoylamino)benzoylamino]ethanoic acid. (compound 10)

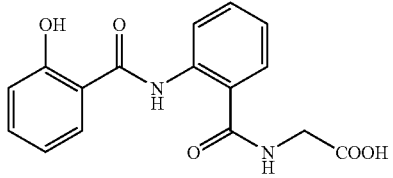

(compound 10)

To a suspension of 4.74 g (24.44 mmol) of 2-(2-aminobenzoylamino)ethanoic acid in 40 ml of dry methylene chloride, add 5.05 g (4.28 mmol) of trimethylsilyl chloride and allow the reaction to reflux for 5 hours. Then place the flask in an ice bath and add 3.16 g (31.32 mmol) of triethylamine and a solution of 4.13 g (20.88 mmol) of acetylsalicyloyl chloride dissolved in 10 ml of dry methylene chloride. Allow the reaction to stir for 30 minutes in an ice bath and 24 hours at room temperature. Eliminate the solvent at low pressure, add 40 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/H$_2$O). This yields 3.54 g (54%) of 2-[2-(2-hydroxybenzoylamino)benzoylamino]ethanoic acid as a white solid.

M.P.: 222-224° C. IR(ATR): ν 3286, 2978, 1730, 1650, 1627, 1598, 1584, 1526, 1242, 900, 835, 752 cm$^{-1}$ $^1$H-NMR (400 MHz, DMSO): δ3.95 (d, 2 H, J=4.9 Hz, —CH$_2$—), 6.97 (m, 2 H, aromatic), 7.21 (m, 1 H, aromatic), 7.41 (m, 1 H, aromatic), 7.55 (m, 1 H, aromatic), 7.80 (m, 2 H, aromatic), 8.52 (m, 2 H, aromatic), 9.07 (S$_{broad}$, 1H, —NH—CH$_2$—), 11.58 (s, 1 H, —OH), 12.18 (s, 1 H, —COOH), 12.70 (s, 1 H, —NH-Ph) ppm $^{13}$C-NMR (200 MHz, DMSO): δ 41.2, 117.2, 118.0, 119.3, 121.8, 122.3, 123.2, 128.1, 129.3, 131.8, 133.7, 138.1, 157.9, 165.4, 168.4, 171.0 ppm. MS m/z (%): 278 (M$^+$−36, 16), 239 (37) 234 (17), 195 (14), 107 (9), 119 (100), 92 (36), 77 (22) 65 (28), 50 (19) Elemental analysis of C$_{20}$H$_{22}$N$_2$O$_5$ Calculated: % C=61.14; % H=4.49; % N=8.91. Found: % C=60.90; % H=4.42; % N=8.98.

EXAMPLE 11

4-[2-(2-hydroxy-4-nitrobenzoylamino)benzoylamino]butanoic acid. (compound 11)

(compound 11)

To a suspension of 1.00 g (4.50 mmol) of 4-(2-aminobenzoylamino)butanoic acid in 20 ml of dry methylene chloride, add 4.50 g (38.50 mmol) of trimethylsilyl chloride and allow the reaction to reflux for 5 hours. Then place the flask in an ice bath and add 0.58 g (5.70 mmol) of triethylamine and a solution of 0.77 g (38.50 mmol) of 2-hydroxy-4-nitrobenzoyl chloride dissolved in 10 ml of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/H$_2$O). This yields 0.50 g (34%) of 4-[2-(2-hydroxy-4-nitro-benzoylamino)benzoylamino]butanoic acid as a yellow solid.

M.P.: 209-211 C. IR(ATR): ν 3378, 2939,.1702, 1592, 1520, 1449, 1420, 1347, 1326, 1300, 1259, 1232, 1215, 1162, 813, 748, 737 cm$^{-1}$ $^1$H-NMR (400 MHz, DMSO): δ1.75 (m, 2 H, —CH$_2$—CH$_2$—CH$_2$—), 2.28 (t, 1 H, J=7.3 Hz, —CH$_2$CO—), 3.26 (m, 2 H, —CH$_2$—N—), 7.20 (m, 1 H, aromatic), 7.52 (m, 1 H, aromatic), 7.66 (m, 1 H, aromatic), 7.74 (m, 2 H, aromatic), 8.10 (m, 1 H, aromatic), 8.49 (m, 1H, aromatic), 8.71 (t, J=5.4 Hz, —NH—CH$_2$—), 12.12 (s, 2 H, —OH, —COOH), 12.30 (s, 1H, —NH) ppm $^{13}$C-NMR (200 MHz, DMSO): δ 24.2, 31.1, 38.7, 111.4, 113.6, 121.1, 123.5, 124.0, 125.4, 128.1, 131.2 132.1, 137.4, 149.9, 156.8, 162.5, 167.8, 174.2 ppm MS m/z (%): 284 (M$^+$−103, 55), 253 (4), 238 (16), 222 (1), 211 (2), 182 (8), 154 (9), 146 (13), 119 (90), 92 (47), 63 (48), 53 (21), 30 (100) Elemental analysis of C$_{18}$H$_{17}$N$_3$O$_7$ Calculated: % C=55.81; % H=4.42; % N=10.85. Found: % C=55.79; % H=4.44; % N=10.74.

EXAMPLE 12

4-[2-(2-hydroxy-5-nitrobenzoylamino)benzoylamino]butanoic acid. (compound 12)

(compound 12)

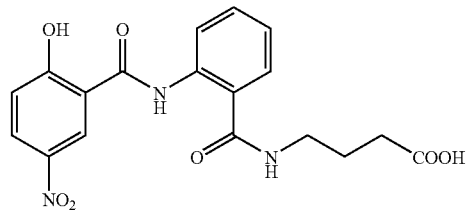

To a suspension of 1.00 g (4.50 mmol) of 4-(2-aminobenzoylamino)butanoic acid in 20 ml of dry methylene chloride, add 4.50 g (38.50 mmol) of trimethylsilyl chloride and allow the reaction to reflux for 5 hours. Then place the flask in an ice bath and add 0.58 g (5.70 mmol) of triethylamine and a solution of 0.77 g (38.50 mmol) of 2-hydroxy-5-nitrobenzoyl chloride dissolved in 10 ml of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and with ether. Purify the reaction product by recrystallization in dioxane/H$_2$O. This yields 0.99 g (67%) of 4-[2-(2-hydroxy-5-nitrobenzoylamino)benzoylamino]butanoic acid as a cream-coloured solid.

M.P.: 239-241° C. IR(ATR): ν3315, 3079, 2626, 1695, 1651, 1631, 1584, 1373, 1334, 1218, 831, 756, 746 cm$^{-1}$ $^1$H-NMR (400 MHz, DMSO): δ1.75 (m, 2 H, —CH$_2$—CH$_2$—CH$_2$—), 2.28 (t, 1 H, J=6.8 Hz, —CH$_2$—CO—), 3.26 (m, 2 H, —CH$_2$—N—), 7.15 (m, 1 H, aromatic), 7.18 (m, 1 H, aromatic), 7.53 (m, 1 H, aromatic), 7.65 (m, 1 H, aromatic), 7.26 (m, 1 H, aromatic), 8.45 (m, 1 H, aromatic), 8.70 (m, J=5.4 Hz, —NH—CH$_2$—), 8.76 (m, 1 H, aromatic), 12.09 (s, 2 H, —OH, —COOH), 12.90 (s, 1 H, —NH) ppm $^{13}$C-NMR (200 MHz, DMSO): δ 24.2, 31.1, 38.7, 117.9, 119.8, 122.2, 123.5, 124.3, 127.2, 128.1, 128.5, 131.1, 137.3, 139.7, 162.0. 162.3, 167.8, 174.2 ppm MS m/z (%): 369 (M$^+$–18, 1), 352 (10), 335 (1), 311 (3), 296 (3), 284 (31), 253 (11), 237 (3), 209 (6), 166 (6), 137 (8), 119 (74), 92 (55), 63 (43), 42 (56), 41 (72), 30 (100) Elemental analysis of C$_{18}$H$_{17}$N$_3$O$_7$ Calculated: % C=55.81; % H=4.42; % N=10.85. Found: % C=55.89; % H=4.50; % N=10.80.

EXAMPLE 13

4-[2-(2-hydroxy-4-methoxybenzoylamino)benzoylamino]butanoic acid. (compound 13)

(compound 13)

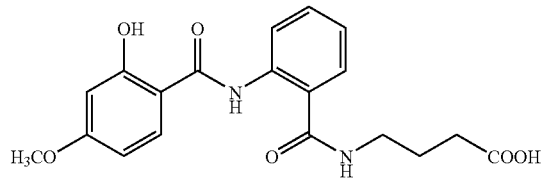

To a suspension of 1.00 g (4.50 mmol) of 4-(2-aminobenzoylamino)butanoic acid in 20 ml of dry methylene chloride, add 4.50 g (38.50 mmol) of trimethylsilyl chloride and allow the reaction to reflux for 5 hours. Then place the flask in an ice bath and add 0.58 g (5.70 mmol) of triethylamine and a solution of 0.71 g (38.5 mmol) of 2-hydroxy-4-methoxybenzoyl chloride dissolved in 10 ml of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/H$_2$O). This yields 0.54 g (38%) of 4-[2-(2-hydroxy-4-methoxybenzoylamino)benzoylamino]butanoic acid as a white solid.

M.P.: 201-203° C. IR(ATR): ν 3306, 2939, 1711, 1643, 1622, 1582, 1524, 1508, 1438, 1383, 1244, 1208, 1178, 1144, 964, 830, 751, 671 cm$^{-1}$ $^1$H-NMR (400 MHz, DMSO): δ 1.76 (m, 2 H, —CH$_2$—CH$_2$—CH$_2$—), 2.29 (t, 1 H, J=7.3 Hz, —CH$_2$—CO—), 3.29 (m, 2 H, —CH$_2$—), 3.78 (s, 3 H, —CH$_3$), 6.48 (m, 1 H, aromatic), 6.58 (m, 1 H, aromatic), 7.17 (m, 1 H, aromatic), 7.50 (m, 1 H, aromatic), 7.71 (m, 1 H, aromatic), 7.76 (m, 1 H, aromatic), 8.45 (m, 1 H, aromatic), 8.77 (t, J=5.4 Hz, —NH—CH$_2$—),12.05 (s, 2 H, —OH, —NH), 12.22 (s, 1 H, —COOH) ppm $^{13}$C-NMR (200 MHz, DMSO): δ 24.2, 31.1, 38.7, 55.4, 101.3, 106.7, 109.9, 121.5, 122.6, 122.9, 128.1, 129.9, 131.5, 138.1, 160.9, 163.8, 166.0, 168.2, 174.2 ppm MS m/z (%): 372 (M$^+$, 3), 353 (2), 269 (84), 228 (16), 222 (17), 182 (4), 151 (100), 120 (58), 119 (59), 92 (47), 65 (24), 52 (12), 30 (53) Elemental analysis of C$_{19}$H$_{20}$N$_2$O$_6$ Calculated: % C=61.28; % H=5.41; % N=7.52. Found: % C=60.89; % H=5.37; % N=7.40.

EXAMPLE 14

4-[2-(2-hydroxy-5-methoxybenzoylamino)benzoylamino]butanoic acid. (compound 14)

(compound 14)

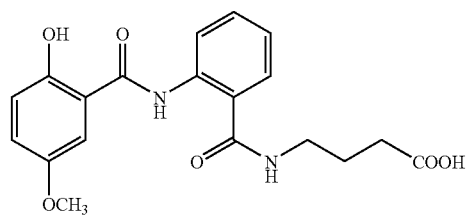

To a suspension of 1.00 g (4.50 mmol) of 4-(2-aminobenzoylamino)butanoic acid in 20 ml of dry methylene chloride, add 4.50 g (38.50 mmol) of trimethylsilyl chloride and allow the reaction to reflux for 5 hours. Then place the flask in an ice bath and add 0.58 g (5.70 mmol) of triethylamine and a solution of 0.71 g (38.5 mmol) of 2-hydroxy-5-methoxybenzoyl chloride dissolved in 10 mL of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/H$_2$O). This yields 0.791 g (56%) of 4-[2-(2-hydroxy-5-methoxybenzoylamino)benzoylamino]butanoic acid as a cream-coloured solid.

M.P.: 191-193° C. IR(ATR): ν 3330, 2877, 1702, 1593, 1523, 1494, 1473, 1449, 1419, 1356, 1328, 1306, 1266, 1205, 1188, 1174, 1047, 931, 792, 746, 687 cm$^{-1}$ $^1$H-NMR (400 MHz, DMSO): δ 1.76 (m, 2 H, —CH$_2$—CH$_2$CH$_2$—), 2.28 (t, 1 H, J=7.3 Hz, —CH$_2$—CO—), 3.27 (m, 2 H, —CH$_2$—), 3.73 (s, 3 H, —CH$_3$), 6.91 (m, 1 H, aromatic), 7.04 (m, 1 H, aromatic), 7.18 (m, 1 H, aromatic), 7.38 (m, 1 H, aromatic), 7.50 (m, 1 H, aromatic), 7.76 (m, 1 H, aromatic), 8.46 (m, 1 H, aromatic), 8.70 (t, J=5.4 Hz, —NH—CH$_2$—), 11.10 (s, 1 H, —OH), 12.03 (s, 1 H, —NH), 12.09 (s, 1 H, —COOH) ppm $^{13}$C-NMR (200 MHz, DMSO): δ 24.2, 31.1, 38.7, 55.4, 112.8, 118.1, 118.3, 120.5, 121.7, 123.1, 123.8, 128.0, 131.2, 137.7, 151.6, 151.9, 164.8, 168.0, 174.2 ppm MS m/z (%): 372 (M$^+$, 5), 353 (3), 269 (100), 254 (88), 198 (11), 150 (20), 120 (55), 119 (45), 92 (50), 79 (33), 65 (29), 52 (21), 30 (51) Elemental analysis of C$_{19}$H$_{20}$N$_2$O$_6$ Calculated: % C=61.28; % H=5.41; % N=7.52. Found: % C=61.21; % H=5.40; % N=7.47.

EXAMPLE 15

4-[2-(4-nitrobenzoylamino)benzoylamino]butanoic acid. (compound 15)

(compound 15)

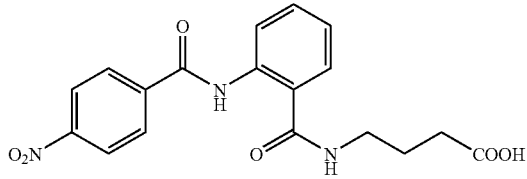

To a suspension of 2.14 g (9.63 mmol) of 4-(2-aminobenzoylamino)butanoic acid in 40 ml of dry methylene chloride, add 1.83 g (16.87 mmol) of trimethylsilyl chloride and allow the reaction to reflux for 5 hours. Then place the flask in an ice bath and add 1.24 g (12.33 mmol) of triethylamine and a suspension of 1.53 g (8.22 mmol) of 4-nitrobenzoyl chloride in 10 ml of dry ethyl acetate. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and with ether. Purify the reaction product by recrystallization in dioxane/$H_2O$. This yields 1.33 g (43%) of 4-[2-(4-nitrobenzoylamino) benzoylamino] butanoic acid as a cream-coloured solid.

M.P.: 206-208 C. IR(ATR): ν 3282, 3090, 1731, 1655, 1626, 1597, 1558, 1517, 1444, 1417, 1399, 1350, 1326, 1297, 1258, 1227, 1166, 854, 836, 766, 715 $cm^{-1}$ $^1$H-NMR (400 MHz, DMSO): δ 1.77 (m, 2 H, —$CH_2$—$CH_2$—$CH_2$—), 2.29 (t, 1 H, J=7.3 Hz, —$CH_2$—CO—), 3.31 (m, 2 H, —$CH_2$—N—), 7.24 (m, 1 H, aromatic), 7.58 (m, 1 H, aromatic), 7.85 (m, 1 H, aromatic), 8.14 (d, 2 H, J=8.7 Hz, aromatic), 8.42 (d, 2 H, J=8.7 Hz, aromatic), 8.58 (m, 1 H, aromatic), 8.46 (m, 1 H, aromatic), 8.91 (t, J=5.4 Hz, —NH—$CH_2$—), 12.06 (s, 1 H, —NH), 12.72 (s, 1 H, —COOH) ppm $^{13}$C-NMR (200 MHz, DMSO): δ 24.1, 31.0, 38.9, 120.5, 120.8, 123.4, 124.1, 128.2, 128.5, 132.2, 138.8, 140.1, 149.4, 162.7, 168.5, 174.2 ppm MS m/z (%): 371 ($M^+$, 5), 353 (3), 334 (1), 269 (22), 268 (29), 253 (6), 238 (59), 224 (9), 150 (23), 146 (23), 120 (50), 119 (100), 104 (39), 92 (69 ), 76 (48), 64 (29), 50 (27), 30 (50) Elemental analysis of $C_{18}H_{17}N_3O_6$ Calculated: % C=58.22; % H=4.61; % N=11.32. Found: % C=58.15; % H=4.65; % N=11.10.

EXAMPLE 16

4-[2-(4-methoxybenzoilamino)benzoilamino]butanoic acid. (compound 16)

(compound 16)

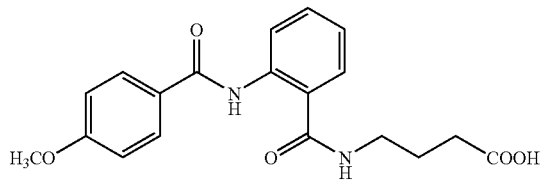

To a suspension of 2.14 g (9.63 mmol) of 4-(2-aminobenzoylamino)butanoic acid in 20 ml of dry methylene chloride, add 8.90 g (82.39 mmol) of trimethylsilyl chloride and place the reaction at reflux for 5 hours. Then place the flask in an ice bath and add 1.25 g (12.36 mmol) of triethylamine and a solution of 1.40 g (8.24 mmol) of 4-methoxybenzoyl chloride dissolved 10 ml of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/$H_2O$). This yields 2.32 g (79%) of 4-[2-(4-methoxybenzoylamino)benzoylamino]butanoic acid as a cream-coloured solid.

M.P.: 172-174° C. IR(ATR): ν 3320, 2960, 2837, 1720, 1630, 1592, 1532, 1509, 1446, 1301, 1254, 1167, 1096, 1025, 841, 748 $cm^{-1}$ $^1$H-NMR (400 MHz, DMSO): δ 1.79 (m, 1 H, —$CH_1$—$CH2_1$—$CH2_1$—), 2.31 (t, 0H, J=7.4 Hz, —$CH2_1$—CO—), 3.33 (m, 1 H, —$CH2_1$—N—), 3.83 (s, 2 H, —$CH_2$—), 7.11 (d, 1 H, J=8.8 Hz aromatic), 7.16 (m, 0H, aromatic), 7.53 (m, 0H, aromatic), 9 (m, 1 H, aromatic), 7.89 (d, 2 H, J=8.8 Hz, aromatic), 8.65 (m, 1 H, aromatic), 8.87 (t, J=5.4 Hz, —NH—$CH3_2$—), 12.08 (s, 1 H, —NH), 12.49 (s, 1 H, —COOH) ppm $^{13}$C-NMR (100 MHz, DMSO): δ 24.2, 31.1, 38.7, 55.5, 114.2, 120.0, 120.1, 122.4, 126.7, 128.2, 128.8, 132.1, 139.7, 162.2, 163.9, 168.7, 174.2 ppm MS m/z (%): 356 ($M^+$, 4), 338 (9), 319 (3), 253 (19), 252 (18), 238 (5), 209 (5), 135 (100), 119 (35), 107 (7), 92 (22), 74 (28), 64 (11), 50 (7), 41 (10) Elemental analysis of $C_{19}H_{20}N_2O_5$ Calculated: % C=64.04; % H=5.66; % N=7.86. Found: % C=63.97; % H=5.63; % N=7.79.

EXAMPLE 17

4-[2-(4-chlorobenzoylamino)benzoylamino]butanoic acid. (compound 17)

(compound 17)

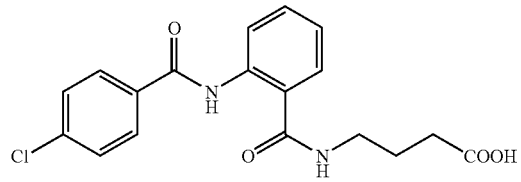

To a suspension of 2.00 g (9.01 mmol) of 4-(2-aminobenzoylamino)butanoic acid in 20 ml of dry methylene chloride, add 8.36 g (77.00 mmol) of trimethylsilyl chloride and allow the reaction to reflux for 5 hours. Then place the flask in an ice bath and add 1.17 g (11.55 mmol) of triethylamine and a solution of 1.35 g (7.70 mmol) of 4-methoxybenzoyl chloride dissolved 10 ml of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/$H_2O$). This yields 1.79 g (65%) of 4-[2-(4-chlorobenzoylamino)benzoylamino]butanoic acid as a cream-coloured solid.

M.P.: 182-184° C. IR(ATR): ν 3069, 2939, 1692, 1672, 1628, 1592, 1525, 1491, 1444, 1332, 1310, 1284, 1259, 1222, 1180, 1110, 1096, 1011, 902, 845, 756, 745 $cm^{-1}$ $^1$H-NMR (400 MHz, DMSO): δ 1.79 (m, 2 H, —$CH_2$—$CH_2$—$CH_2$—), 2.31 (t, 1 H, J=7.4 Hz, —$CH_2$—CO—), 3.32 (m, 2 H,

—CH$_2$—N—), 7.18 (m, 1 H, aromatic), 7.54 (m, 1 H, aromatic), 7.64 (d, 2 H, J=8.5 Hz, aromatic), 7.83 (m, 1 H, aromatic), 7.92 (d, 2 H, J=8.5 Hz, aromatic), 8.61 (m, 1 H, aromatic), 8.89 (t, J=5.4 Hz, —NH—CH$_2$), 12.07 (s, 1 H, —NH), 12.61 (s, 1 H, —COOH) ppm $^{13}$C-NMR (200 MHz, DMSO): δ 24.2, 31.1, 38.7, 55.5, 114.2, 120.3, 120.4, 122.9, 128.2, 128.8, 129.0, 132.2, 133.3 136.9, 139.3, 163.3, 168.6, 174.2 ppm MS m/z (%): 360 (M$^+$, 11), 342 (4), 323 (1), 258 (30), 238 (15), 213 (6), 187 (8), 162 (6), 141 (33), 139 (100), 119 (38), 111 (56), 92 (25), 75 (20), 65 (11), 41 (11) Elemental analysis of C$_{18}$H$_{17}$ClN$_2$O$_4$ Calculated: % C=59.92; % H=4.75; % N=7.76. Found: % C=59.71; % H=4.77; % N=7.72.

EXAMPLE 18

4-[2-(4-chloro-2-hydroxybenzoylamino)benzoylamino]butanoic acid. (compound 18)

(compound 18)

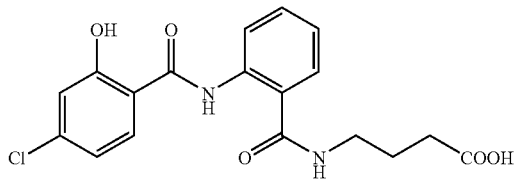

To a suspension of 2.00 g (9.00 mmol) of 4-(2-aminobenzoylamino)butanoic acid in 40 ml of dry methylene chloride, add 8.36 g (77.00 mmol) of trimethylsilyl chloride and allow the reaction to reflux for 5 hours. Then place the flask in an ice bath and add 1.17 g (11.50 mmol) of triethylamine and a solution of 1.45 g (7.70 mmol) of 4-chloro-2-hydroxybenzoyl chloride dissolved in 5 ml of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and ether. Purify the reaction product by recrystallization (EtOH/H$_2$O). This yields 1.35 g (47%) of 4-[2-(4-chloro-2-hydroxybenzoylamino)benzoylamino]butanoic acid as a white solid.

M.P.: 205-206 C. IR(ATR): ν 3319, 3067, 2936, 1688, 1583, 1525, 1494, 1447, 1408, 1350, 1330, 1302, 1261, 1214, 919, 796, 755 cm$^{-1}$ $^1$H-NMR (400 MHz, DMSO): δ 1.75 (m, 2 H, —CH$_2$—CH$_2$—CH$_2$—), 2.28 (t, 2 H, J=7.3 Hz, —CH$_2$—CO—), 3.26 (m, 2 H, —CH$_2$—N—), 7.01 (m, 2 H, aromatic), 7.18 (m, 1 H, aromatic), 7.50 (m, 1 H, aromatic), 7.65 (m, 1 H, aromatic), 7.87 (m, 1 H, aromatic), 8.46 (m, 1H, aromatic), 8.69 (t, 1 H, J=5.12 Hz, —NH—CH$_2$—), 12.07 (S$_{broad}$, 3H, —OH, —COOH, —NH-Ph) ppm $^{13}$C NMR (200 MHz, DMSO): δ 24.3, 31.1, 38.6, 116.6, 117.8, 119.3, 121.9, 123.2, 123.9, 128.0, 131.1, 131.7, 137.3, 137.6, 158.4 163.9, 167.9, 174.2 ppm. MS m/z (%): 376 (M$^+$, 2), 273 (65), 238 (17), 222 (7), 155 (25), 146 (5), 120 (39), 119 (100), 99 (13), 92 (43), 63 (27), 30 (45) Elemental analysis of C$_{18}$H$_{17}$ClN$_2$O$_5$ Calculated: % C=57.38; % H=4.59; % N=7.43. Found: % C=57.19; % H=4.57; % N=7.41.

EXAMPLE 19

4-[2-(5-chloro-2-hydroxybenzoylamino)benzoylamino]butanoic acid. (compound 19)

(compound 19)

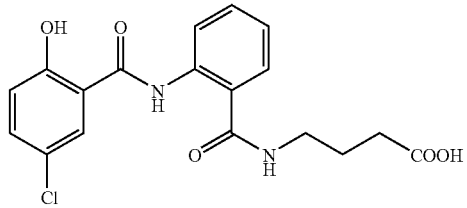

To a suspension of 2.30 g (10.4 mmol) of 4-(2-aminobenzoylamino)butanoic acid in 40 ml of dry methylene chloride, add 9.56 g (88.50 mmol) of trimethylsilyl chloride and allow the reaction to reflux for 5 hours. Then place the flask in an ice bath and add 1.34 g (13.30 mmol) of triethylamine and a solution of 1.67 g (8.85 mmol) of 5-chloro-2-hydroxybenzoyl chloride dissolved in 5 ml of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and with ether. Purify the reaction product by recrystallization (EtOH/H$_2$O). This yields 0.95 g (29%) of 4-[2-(5-chloro-2-hydroxybenzoylamino)benzoylamino]butanoic acid as a white solid.

M.P.: 222-223 C. IR(ATR): ν 3315, 2958, 1693, 1657, 1594, 1524, 1479, 1447, 1360, 1325, 1303, 1272, 1213, 914, 812, 749 cm$^{-1}$ $^1$H-NMR (400 MHz, DMSO): δ 1.75 (m, 2 H, —CH$_2$—CH$_2$—CH$_2$—), 2.28 (t, 2 H, J=7.3 Hz, —CH$_2$—CO—), 3.26 (m, 2 H, —CH$_2$—N—), 7.01 (m, 2 H, aromatic), 7.18 (m, 1 H, aromatic), 7.50 (m, 1 H, aromatic), 7.50 (m, 1 H, aromatic), 7.63 (m, 1 H, aromatic), 7.83 (m, 1H, aromatic), 8.43 (m, 1 H, aromatic), 8.67 (t, 1 H, J=5.5 Hz, —NH—CH$_2$—), 11.99 (S$_{broad}$, 3H, —OH, —COOH, —NH-Ph) ppm $^{13}$C NMR (200 MHz, DMSO): δ 24.2, 31.1, 38.6, 118.9, 120.5, 122.3, 122.8, 123.3, 124.3, 128.0, 129.4, 131.6, 132.9, 137.4, 155.8, 163.1, 167.8, 174.2 ppm. MS m/z (%): 376 (M$^+$, 3), 273 (100), 238 (22), 155 (18), 120 (40), 119 (80), 99 (13), 92 (46), 63 (26), 30 (35) Elemental analysis of C$_{18}$H$_{17}$ClN$_2$O$_5$ Calculated: % C=57.38; % H=4.59; % N=7.43. Found: % C=57.27; % H=4.58; % N=7.41.

EXAMPLE 20

4-[2-(2-chlorobenzoylamino)benzoylamino]butanoic acid. (compound 20)

(compound 20)

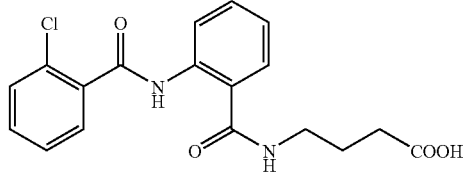

To a suspension of 2.00 g (9.01 mmol) of 4-(2-aminobenzoylamino)butanoic acid in 20 mL of dry methylene chloride, add 8.36 g (77.00 mmol) of trimethylsilyl chloride and allow the reaction to reflux for 5 hours. Then place the flask in an ice bath and add 1.17 g (11.55 mmol) of triethylamine and a solution of 1.35 g (7.70 mmol) of 2-chlorobenzoyl chloride dissolved in 5 mL of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl and extract several times with ethyl acetate. Dry the organic phase with $MgSO_4$ anhydrous and eliminate at low pressure. Wash the crude product several times with ether and finally, purify by recrystallization (EtOH/$H_2O$). This yields 1.27 g (36%) of 4-[2-(2-chlorobenzoylamino)benzoylamino]butanoic acid as a brown solid.

M.P.: 110-112° C. IR(ATR): ν 3308, 1730, 1659, 1627, 1598, 1560, 1513, 1445, 1433, 1310, 1287, 1255, 1168 $cm^{-1}$ $^1$H-NMR (400 MHz, DMSO): δ 1.73 (m, 2 H, —$CH_2$—$CH_2$—$CH_2$—), 2.26 (t, 2 H, J=7.0 Hz, —$CH_2$—CO—), 3.24 (m, 2 H, —$CH_2$—N—), 7.21 (m, 1 H, aromatic), 7.51 (m, 4H, aromatic), 7.65 (m, 1 H, aromatic), 7.79 (m, 1 H, aromatic), 8.53 (m, 1 H, aromatic), 8.82 ($S_{broad}$, 1H, —NH—$CH_2$—), 11.89 (s, 1 H, —COOH), 12.05 (s, 1 H, —NH) ppm $^{13}$C NMR (100 MHz, DMSO): δ 24.1, 31.1, 38.6, 120.4, 121.1, 123.3, 127.6, 128.2, 128.9, 129.8, 130.2, 131.7, 132.0, 136.3, 138.5, 164.3, 168.2, 174.1 ppm. MS m/z (%): 360 ($M^+$, 1), 342 (7), 289 (9), 269 (8), 257 (50), 213 (57), 178 (16), 139 (97) 120 (22), 119 (100), 111 (60), 85 (67), 75 (81), 63 (32), 50 (63), 30 (76) Elemental analysis of $C_{18}H_{17}ClN_2O_4$ Calculated: % C=59.92; % H=4.75; N=7.76. Found: % C=59.95; % H=4.77; % N=7.68.

EXAMPLE 21

4-[2-(2-bromobenzoylamino)benzoylamino]butanoic acid. (compound 21)

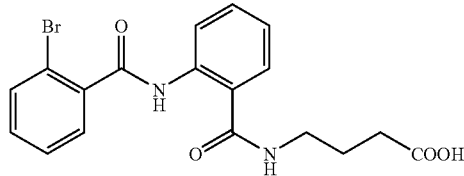

(compound 21)

To a suspension of 2.00 g (9.01 mmol) of 4-(2-aminobenzoylamino)butanoic acid in 20 mL of dry methylene chloride, add 8.36 g (77.00 mmol) of trimethylsilyl chloride and allow the reaction to reflux for 5 hours. Then place the flask in an ice bath and add 1.17 g (11.55 mmol) of triethylamine and a solution of 1.68 g (7.70 mmol) of 2-bromobenzoyl chloride dissolved in 5 mL of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl, filter the resulting solid and wash several times with water and with ether. Finally, purify by recrystallization (EtOH/$H_2O$). This yields 1.95 g (63%) of 4-[2-(2-bromobenzoylamino)benzoylamino] butanoic acid as a cream-coloured solid.

M.P.: 117-118° C. IR(ATR): ν 3280, 3176, 1731, 1654, 1628, 1598, 1557, 1510, 1444, 1428, 1312, 1286, 1251, 1166, 743, 664 $cm^{-1}$ $^1$H-NMR (400 MHz, DMSO): δ1.74 (m, 2 H, —$CH_2$—$CH_2CH_2$—), 2.26 (t, 2 H, J=7.3 Hz, —$CH_2$—CO—), 3.23 (m, 2 H, —$CH_2$—N—), 7.21 (m, 1 H, aromatic), 7.45 (m, 1 H, aromatic), 7.53 (m, 2 H, aromatic), 7.61 (m, 1 H, aromatic), 8.53 (m, 1 H, aromatic), 8.81 (t, 1 H, J=5.28 Hz, —NH—$CH_2$—), 11.84 (s, 1 H, —COOH), 12.03 (s, 1 H, —NH) ppm $^{13}$C NMR (100 MHz, DMSO): δ 24.1, 31.1, 38.6, 118.6, 120.4, 121.1, 123.3, 128.1, 128.2, 128.7, 131.7, 132.0, 133.2, 138.5, 138.6, 165.2, 168.1, 174.2 ppm. MS $C_{18}H_{17}N_2O_4{}^{79}$Br m/z (%): 404 ($M^+$, 1), 303 (32), 257 (20), 238 (20), 221 (22), 185 (100), 178 (12), 157 (31) 143 (26), 119 (60), 90 (31), 76 (41), 50 (39) Elemental analysis of $C_{18}H_{17}BrN_2O_4$ Calculated: % C=53.35; % H=4.23; N=6.91. Found: % C=53.32; % H=4.26; % N=6.89.

EXAMPLE 22

4-[2-(3-chlorobenzoylamino)benzoylamino]butanoic acid. (compound 22)

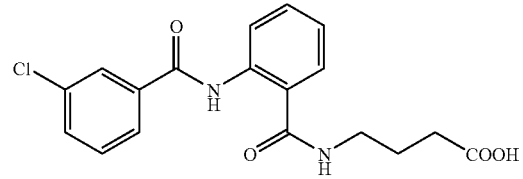

(compound 22)

To a suspension of 2.00 g (9.01 mmol) of 4-(2-aminobenzoylamino)butanoic acid in 20 mL of dry methylene chloride, add 8.36 g (77.00 mmol) of trimethylsilyl chloride and allow the reaction to reflux for 5 hours. Then place the flask in an ice bath and add 1.17 g (11.55 mmol) of triethylamine and a solution of 1.35 g (7.70 mmol) of 3-chlorobenzoyl chloride dissolved in 5 mL of dry methylene chloride. Allow the reaction to stir for 30 minutes in an ice bath and 24 hours at room temperature. Eliminate the solvent at low pressure, add 30 ml of 10% NaOH to the crude product and continue stirring the mixture until the oil has completely disappeared. Immediately acidify with concentrated HCl and extract several times with ethyl acetate. Dry the organic phase with $MgSO_4$ anhydrous and eliminate at low pressure. Wash the crude product several times with ether and finally, purify by recrystallization (EtOH/$H_2O$). This yields 0.83 g (30%) of 4-[2-(3-chlorobenzoylamino)benzoylamino]butanoic acid as a cream-coloured solid.

M.P.: 165-166° C. IR(ATR): ν 3307, 3159, 1741, 1721, 1669, 1626, 1589, 1523, 1447, 1419, 1326, 1308, 1256, 1180, 759 $cm^{-1}$ $^1$H-NMR (400 MHz, DMSO): δ1.78 (m, 2 H, —$CH_2$—$CH_2$—$CH_2$—), 2.30 (t, 2 H, J=7.0 Hz, —$CH_2$—CO—), 3.30 (m, 2 H, —$CH_2$—N—), 7.21 (m, 1 H, aromatic), 7.56 (m, 1 H, aromatic), 7.65 (m, 1 H, aromatic), 7.71 (m, 1 H, aromatic), 7.84 (m, 2 H, aromatic), 7.91 (m, 1H, aromatic), 8.57 (m, 1 H, aromatic), 8.88 (t, 1 H, J=5.3 Hz, —NH—$CH_2$—), 12.05 (s, 1H, —COOH), 12.57 (s, 1 H, -Ph-NH) ppm $^{13}$C NMR (100 MHz, DMSO): δ 24.1, 31.1, 38.6, 120.4, 121.1, 123.3, 127.6, 128.2, 128.9, 129.8, 130.2, 131.7, 132.0, 136.3, 138.5, 164.3, 168.2, 174.1 ppm. MS m/z (%): 360 ($M^+$, 8), 323 (5), 258 (38), 238 (41), 213 (19), 139 (100) 120 (64), 119 (95), 111 (96), 92 (55), 75 (40), 65 (32), 50 (28), 39 (39) Elemental analysis of $C_{18}H_{17}ClN_2O_4$ Calculated: % C=59.92; % H=4.75; % N=7.76. Found: % C=59.87; % H=4.78; % N=7.76.

The activity of all compounds of the examples described above was studied in animals according to the following experimental model:

1. Purpose and Rationale

Evaluate the absorption of the test product when administered by intracolonic route to rats, whether or not in the presence of adjuvants. The plasma concentration is measured by assaying the Factor Xa-inhibition capacity. The rat is used because it is one of the species commonly used in this type of test.

2. Description of the Test Method 2.1. Experimental System

| Description: | Wistar male rats, acquired from an accredited supplier. |
|---|---|
| Weight | 200-250 g |
| Age | 9 to 11 weeks |

2.2. Mode of Administration

One intracolonic administration.

2.3. Dosage Levels and Administration Volume

| Dosage level | 30 mg/kg of test product + 30 mg/kg of adjuvant |
|---|---|
| Administration volume | 1 ml/kg |

2.4. Vehicle

25% (v/v) propylene glycol in bidistilled water. After dissolving the test product along with the adjuvant if applicable, adjust the pH to approximately 7.4 with NaOH.

3.5. Experimental Design

The animals will be in fasted state for approximately 18 h with free access to water The animals will be randomized to the various experimental groups, with one remaining animal as a reserve per group:

On the day of the test, the treatments will be administered by intracolonic route, following anaesthesia with ketamine. Administration will be done using a catheter of approximately 8 cm, connected to a 1-ml syringe. The catheter will be introduced in its entirety into the colon through the anus and the test product will be administered slowly into the colon.

Following the administration of the test product, within the times established in the table, a citrated blood sample (3.8% at a ratio of 1:9) will be drawn by intracardiac puncture under anaesthesia with ketamine.

Blood centrifugation: 3000 rpm, 10 minutes, 4° C. Plasma freezing (−20±5° C.) until determining the anti-Factor Xa activity.

A control group that will receive no treatment will be included, simply that one blood sample will be drawn per animal under the same conditions as the treatment group, with considered to be the baseline value of anti-Xa activity.

The anti-Xa activity will be assayed by the chromogenic method (anti-FXa activity assay kit).

3. Evaluation of the Results

The mean, the standard deviation (RSD) and the standard error of the mean of each experimental group will be calculated for each parameter. If considered adequate, the values obtained in the different experimental groups will be compared by a statistical analysis.

The invention claimed is:

1. Amino acid diamides in non-α position of formula (1)

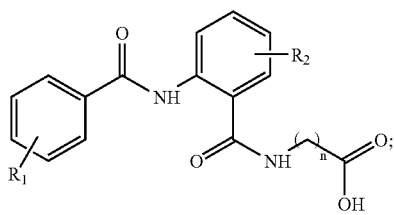

(1)

where in: n = 2 to 8

$R_1$ is selected from the group consisting of halogen, $NO_2$, OH, $OCH_3$ and a combination thereof; and $R_2$ is selected from the group consisting of H, alkyl, halogen, $NO_2$, OH, and $OCH_3$.

2. Diamides according to claim 1 comprising:

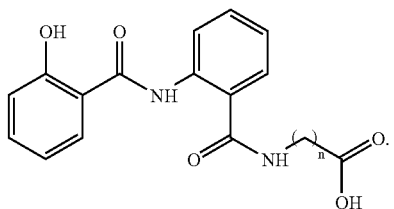

(2)

where in: n = 2 to 8

3. Diamides according to claim 1 comprising:

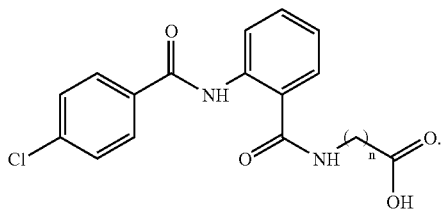

(3)

where in n = 2 to 8

4. Compounds according to claim 1, wherein they present the following structure:

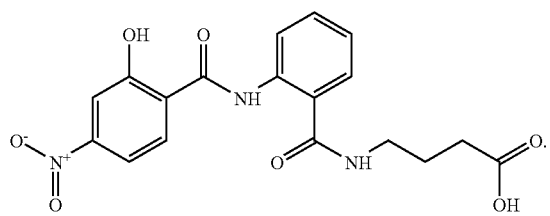

(4)

5. A pharmaceutical composition comprising heparin oligosaccharides and at least one compound according to claim 1.

6. A pharmaceutical composition comprising at least one compound according to claim 2 and glycosaminoglycan oligosaccharides.

7. A pharmaceutical composition comprising at least one compound according to claim 3 and glycosaminoglycan oligosaccharides.

8. A pharmaceutical composition comprising at least one compound according to claim 4 and glycosaminoglycan oligosaccharides.

9. A pharmaceutical composition according to claim 5, comprising

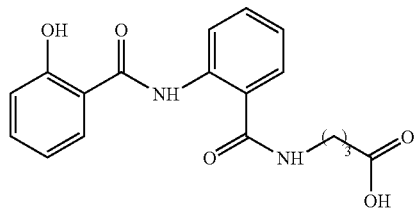

and Bemiparin.

10. A pharmaceutical composition according to claim 5 comprising

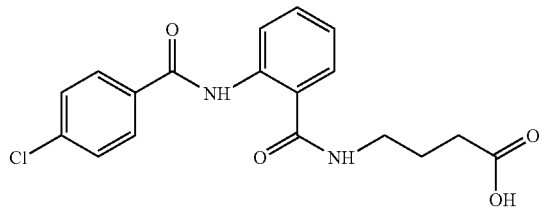

and Bemiparin.

11. A pharmaceutical composition according to claim 5 comprising

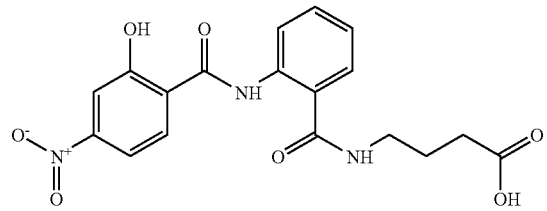

and Bemiparin.

12. A pharmaceutical composition according to claim 1 at least one compound according to formula (1) and at least one active agent selected from the group consisting of heparin, dermatan sulphate, condroitin sulphate, heparan sulphate and oligosaccharide derivatives.

13. A method of enhancing the colonic absorption of a glycosaminoglycan or glycosaminoglycan oligosaccharide following administration thereof, the method comprising:

orally or intracolonically administering to a subject in need thereof a compound according to any one of claims 1-4 or 5 and a glycosaminoglycan or glycosaminoglycan oligosaccharide thereby enhancing the colonic absorption of the glycosaminoglycan or glycosaminoglycan oligosaccharide.

14. A method of treating thrombosis comprising:

administering to a subject in need thereof a compound according to any one of claims 1-4 or 5 and a glycosaminoglycan or glycosaminoglycan oligosaccharide.

15. The method of claim 14, wherein the step of administering is selected from the group consisting of oral, intraduodenal, intracolonic and pulmonary administration.

* * * * *